(12) United States Patent  (10) Patent No.: US 9,478,327 B2
Walsh et al.  (45) Date of Patent: *Oct. 25, 2016

(54) DURABLE FINE WIRE ELECTRICAL CONDUCTOR SUITABLE FOR EXTREME ENVIRONMENT APPLICATIONS

(71) Applicant: NuAx, Inc., Minnetonka, MN (US)

(72) Inventors: Robert G. Walsh, Newport, OR (US); Jin Shimada, Grantsburg, WI (US); Scott Engle, Independence, MN (US)

(73) Assignee: NuAx, Inc., Minnetonka, MN (US)

( * ) Notice: Subject to any disclaimer, the term of this patent is extended or adjusted under 35 U.S.C. 154(b) by 32 days.

This patent is subject to a terminal disclaimer.

(21) Appl. No.: 14/184,580

(22) Filed: Feb. 19, 2014

(65) Prior Publication Data

US 2015/0262733 A1  Sep. 17, 2015

Related U.S. Application Data

(63) Continuation of application No. 12/804,271, filed on Jul. 16, 2010, now Pat. No. 8,692,117, which is a continuation-in-part of application No. 12/156,129, filed on May 28, 2008, now abandoned, and a (Continued)

(51) Int. Cl.
*H01B 9/00* (2006.01)
*A61N 1/05* (2006.01)
(Continued)

(52) U.S. Cl.
CPC .... *H01B 9/005* (2013.01); *A61N 1/05* (2013.01); *A61N 1/056* (2013.01); *H01B 1/14* (2013.01); *H01B 1/18* (2013.01); *H01B 7/04* (2013.01); *H01B 7/048* (2013.01); *A61N 1/0551* (2013.01)

(58) Field of Classification Search
CPC ............ H01B 3/42; H01B 3/00; H01B 11/16; H01B 11/00; H01B 7/04; H01B 7/048; A61N 1/05; A61N 1/056; A61N 1/057; A61N 1/0504; G02B 6/3817; G02B 6/4415; G02B 6/4416
USPC ........... 174/70 R, 126.1, 126.4, 126.2, 110 R, 174/113 R, 113 C, 120 R, 121 R, 122 R, 174/122 C, 120 SR, 124 R, 110 SR; 607/5, 607/115–116, 119, 122
See application file for complete search history.

(56) References Cited

U.S. PATENT DOCUMENTS 3,980,806 A  9/1976 May
4,276,144 A  6/1981 Hahn
(Continued)

*Primary Examiner* — Dimary Lopez Cruz
(74) *Attorney, Agent, or Firm* — John M. Berns

(57) ABSTRACT

Durable fine wire electrical conductors are robust, durable, small in profile, and light weight, yet capable of operating under extreme environmental conditions. Formed of a glass, silica, sapphire or crystalline quartz fiber core with a metal coating and one or more polymer layers, a unipolar electrical conductor can have an outer diameter as small as about 300 microns or even smaller. The metal buffer coating may be deposited directly on the glass/silica fiber, or upon an intermediate layer between the glass/silica fiber and metal, consisting of carbon and/or polymer. The resulting metallized glass/silica fibers are extremely durable, can be bent through small radii and will not fatigue even from millions of iterations of flexing. Bipolar electrical conductors can include several insulated metallized glass/silica fibers residing side by side, or can be coaxial with two or more insulated metal conductive paths. An outer protective sheath of a flexible polymer material can be included.

20 Claims, 7 Drawing Sheets

Related U.S. Application Data continuation-in-part of application No. 12/590,851, filed on Nov. 12, 2009, now abandoned.

(60) Provisional application No. 61/271,077, filed on Jul. 17, 2009, provisional application No. 61/198,900, filed on Nov. 12, 2008.

(51) Int. Cl.
*H01B 1/14* (2006.01)
*H01B 7/04* (2006.01)
*H01B 1/18* (2006.01)

(56) References Cited

U.S. PATENT DOCUMENTS

| | | | |
|---|---|---|---|
| 4,407,561 A | 10/1983 | Wysocki | |
| 4,408,604 A | 10/1983 | Hirshorn et al. | |
| 4,418,984 A | 12/1983 | Wysocki et al. | |
| 4,575,187 A | 3/1986 | Howard et al. | |
| 4,785,815 A | 11/1988 | Cohen | |
| 4,791,575 A | 12/1988 | Gupta et al. | |
| 4,798,206 A | 1/1989 | Maddison et al. | |
| 4,873,989 A | 10/1989 | Einzig | |
| 4,896,209 A | 1/1990 | Matsuzaki | |
| 4,911,712 A | 3/1990 | Harrington | |
| 5,117,828 A | 6/1992 | Metzger et al. | |
| 5,218,171 A | 6/1993 | Aldissi | |
| 5,433,744 A | 7/1995 | Breyen et al. | |
| 5,463,138 A | 10/1995 | Muller | |
| 5,500,012 A | 3/1996 | Brucker et al. | |
| 5,531,779 A | 7/1996 | Dahl et al. | |
| 5,750,930 A | 5/1998 | Buck et al. | |
| 6,104,961 A | 8/2000 | Conger et al. | |
| 6,129,685 A | 10/2000 | Howard | |
| 6,167,314 A | 12/2000 | Fischer et al. | |
| 6,178,356 B1 | 1/2001 | Chastain et al. | |
| 6,195,411 B1 | 2/2001 | Dinsmore | |
| 6,319,188 B1 | 11/2001 | Lovoi | |
| 6,356,791 B1 | 3/2002 | Westlund et al. | |
| 6,366,819 B1 | 4/2002 | Stokes | |
| 6,456,888 B1 | 9/2002 | Skinner et al. | |
| 6,564,107 B1 | 5/2003 | Bodner et al. | |
| 6,697,676 B2 | 2/2004 | Dahl et al. | |
| 6,711,443 B2 | 3/2004 | Osypka | |
| 6,792,316 B2 | 9/2004 | Sass | |
| 6,849,074 B2 | 2/2005 | Chen et al. | |
| 6,879,861 B2 | 4/2005 | Benz et al. | |
| 6,930,242 B1 | 8/2005 | Helfer et al. | |
| 6,986,766 B2 * | 1/2006 | Caldera | A61B 18/22 128/898 |
| 7,010,356 B2 | 3/2006 | Jog et al. | |
| 7,077,837 B2 | 7/2006 | Sahagian | |
| 7,079,902 B2 | 7/2006 | Soukup et al. | |
| 7,137,395 B2 | 11/2006 | Fried et al. | |
| 7,231,260 B2 | 6/2007 | Wallace et al. | |
| 7,420,124 B2 | 9/2008 | Michael et al. | |
| 7,519,432 B2 | 4/2009 | Bolea et al. | |
| 7,865,044 B2 | 1/2011 | Farhadiroushan et al. | |
| 7,883,536 B1 | 2/2011 | Bendett et al. | |
| 7,917,213 B2 | 3/2011 | Bulkes et al. | |
| 8,000,808 B2 | 8/2011 | Hegland et al. | |
| 2001/0055904 A1 | 12/2001 | Sawada et al. | |
| 2002/0052636 A1 | 5/2002 | Bardy et al. | |
| 2002/0183818 A1 | 12/2002 | Williams et al. | |
| 2002/0189845 A1 | 12/2002 | Gorrell | |
| 2003/0077935 A1 | 4/2003 | Stein et al. | |
| 2003/0195602 A1 | 10/2003 | Boling | |
| 2003/0195603 A1 | 10/2003 | Scheiner | |
| 2004/0024440 A1 | 2/2004 | Cole | |
| 2004/0064174 A1 | 4/2004 | Belden | |
| 2004/0122499 A1 | 6/2004 | Westlund | |
| 2004/0243210 A1 | 12/2004 | Morgan et al. | |
| 2005/0090885 A1 | 4/2005 | Harris et al. | |
| 2005/0096720 A1 | 5/2005 | Sharma et al. | |
| 2005/0103932 A1 | 5/2005 | Huynh | |
| 2006/0009830 A1 | 1/2006 | Atkinson et al. | |
| 2006/0095105 A1 | 5/2006 | Jog et al. | |
| 2006/0106443 A1 | 5/2006 | Michael et al. | |
| 2006/0293741 A1 | 12/2006 | Johnson et al. | |
| 2007/0067000 A1 | 3/2007 | Strother et al. | |
| 2007/0088208 A1 | 4/2007 | Yasuzawa et al. | |
| 2007/0088417 A1 | 4/2007 | Schouenborg | |
| 2007/0288077 A1 | 12/2007 | Bulkes et al. | |
| 2007/0293923 A1 | 12/2007 | Soltis et al. | |
| 2008/0015625 A1 | 1/2008 | Ventura et al. | |
| 2008/0039916 A1 | 2/2008 | Colliou et al. | |
| 2008/0077220 A1 | 3/2008 | Reddy | |
| 2008/0097567 A1 | 4/2008 | Haldeman | |
| 2008/0183257 A1 | 7/2008 | Imran et al. | |
| 2008/0188910 A1 * | 8/2008 | Spaide | 607/89 |
| 2008/0217587 A1 | 9/2008 | Gaudiana et al. | |
| 2008/0255629 A1 | 10/2008 | Jenson et al. | |
| 2009/0204193 A1 | 8/2009 | Kokones et al. | |
| 2009/0299446 A1 | 12/2009 | Lovoi et al. | |
| 2010/0057179 A1 | 3/2010 | Storey | |
| 2010/0114271 A1 | 5/2010 | Sommer et al. | |
| 2010/0182023 A1 | 7/2010 | Pena et al. | |
| 2010/0183269 A1 | 7/2010 | Mahapatra et al. | |
| 2010/0278491 A1 | 11/2010 | Noddings | |
| 2011/0220408 A1 | 9/2011 | Walsh et al. | |
| 2011/0245714 A1 | 10/2011 | Volckaerts | |
| 2011/0301657 A1 | 12/2011 | Walsh et al. | |
| 2012/0277600 A1 | 11/2012 | Greenhut | |
| 2013/0041447 A1 | 2/2013 | Erb et al. | |

* cited by examiner

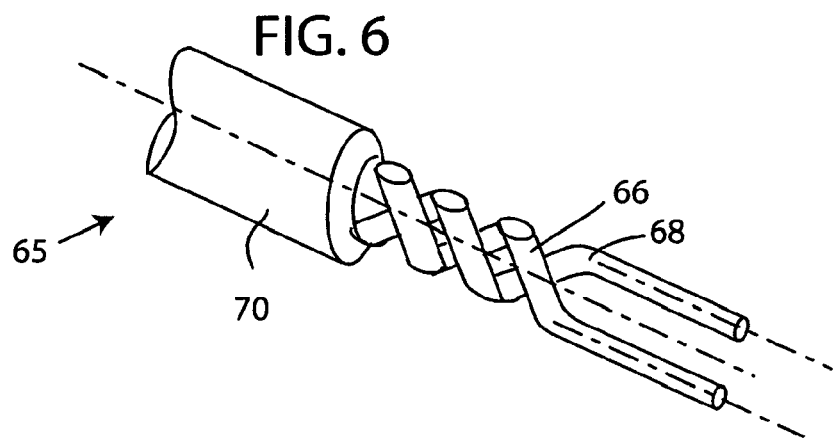
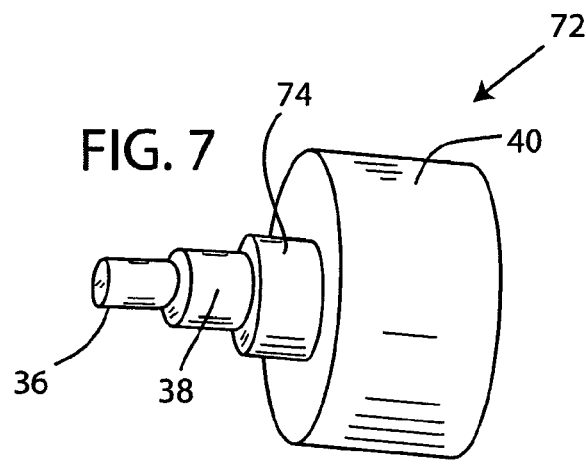
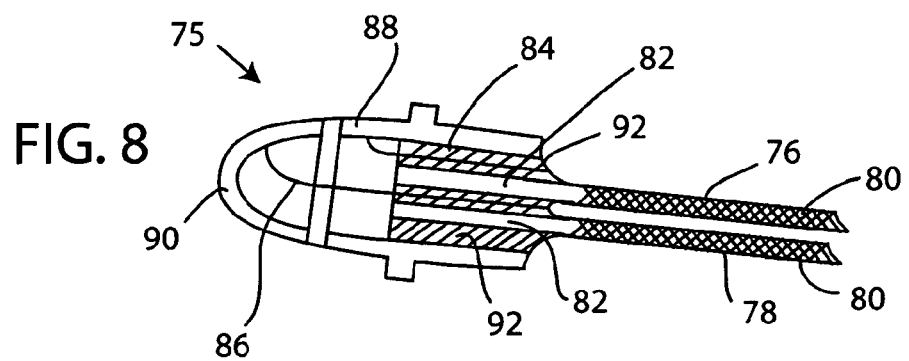

DURABLE FINE WIRE ELECTRICAL CONDUCTOR SUITABLE FOR EXTREME ENVIRONMENT APPLICATIONS

This application claims benefit of priority to U.S. Provisional Application No. 61/271,077, filed Jul. 17, 2009. This application also claims the benefit of priority as a continuation-in-part of U.S. application Ser. No. 12/156,129, filed May 28, 2008, incorporated herein by reference. This application also claims the benefit of priority as a continuation-in-part of U.S. application Ser. No. 12/590,851, filed Nov. 12, 2009 and incorporated herein by reference. This application further claims the benefit of priority as a continuation of U.S. patent application Ser. No. 12/804,271, filed Jul. 16, 2010.

BACKGROUND OF THE INVENTION

This invention concerns an electrical conductor suitable for use under conventional environmental conditions, but more importantly, is also functional and durable upon exposure to extreme environmental conditions. For purposes of this provisional patent application, an extreme environment is characterized by conditions that might include one or more of the following: hot or cold ambient temperatures, chronic vibration or bending, and exposure to aqueous conditions including body tissues, environmental contaminants such as dust, sunlight, or vacuum. Application of the electrical conductor of this patent application may be towards implantable medical devices such as cardiac pacemakers, ICD and CRT devices, and neurostimulation devices, or may be towards various military and civilian non-medical roles including aviation, ground transportation, boats or ships, and aerospace, especially where the conductors will be subjected to vibration or bending or corrosive effects, or where minimizing weight is important.

The ideal characteristics of an electrical conductor for non-medical applications depend on the exact nature of the intended use. Electrical conductors used in benign applications such as providing electrical power throughout a building may consist of a simple copper conductor encased in polymeric insulation. Other non-medical applications may require that electrical conductors function with a great degree of precision and integrity in hostile environments, posing challenges to electrical conductor design that are shared with implantable medical devices. For instance, electrical conductors deployed in environments where the conductor is exposed to repetitive motion may result in fatigue failure to the conductor, not unlike what can occur with pacemaker or defibrillator leads. Non-medical electrical conductors may also be required to operate in wet conditions, which require that insulation be incorporated on the conductor to protect from direct contact with water, not unlike electrical leads of implanted medical devices.

In addition to these similarities, electrical conductors for non-medical applications may also be called upon to operate under extremes of temperature (hot and cold), chronic vibration, sunlight exposure, vacuum, or other environmental factors. These electrical conductors may also need to operate under conditions in which minimization of size and weight are required in ways that are not met by currently available electrical conductors.

As far as medical applications are concerned, cardiac pacing has become a well-tested and effective means of maintaining heart function for patients with various heart conditions. Generally pacing is done from a control unit placed under but near the skin surface for access and communications with the physician controller when needed. Leads are routed from the controller to the heart probes to provide power for pacing and data from the probes to the controller. Probes are generally routed into the heart through the right, low pressure, side of the heart. No left, high pressure, heart access through the heart wall has been successful. For access to the left side of the heart, lead wires are generally routed from the right side of the heart through the coronary sinus and into veins draining the left side of the heart. This access path has several drawbacks; the placement of the probes is limited to areas covered by veins, and the leads occlude a significant fraction of the vein cross section and the number of probes is limited to 1 or 2.

Over 650,000 pacemakers are implanted in patients annually worldwide, including over 280,000 in the United States. Over 3.5 million people in the developed world have implanted pacemakers. Another approximately 900,000 have an ICD or CRT device. The pacemakers involve an average of about 1.4 implanted conductive leads, and the ICD and CRT devices use on average about 2.5 leads. These leads are necessarily implanted through tortuous pathways in the hostile environment of the human body. They are subjected to repeated flexing due to beating of the heart and the muscular movements associated with that beating, and also due to other movements in the upper body of the patient, movements that involve the pathway from the pacemaker to the heart. This can subject the implanted leads, at a series of points along their length, through tens of millions of iterations per year of flexing and unflexing, hundreds of millions over a desired lead lifetime. Previously available wire leads have not withstood these repeated flexings over long periods of time, and many have experienced failure due to the fatigue of repeated bending.

Neurostimulation refers to a therapy in which low voltage electrical stimulation is delivered to the spinal cord or targeted peripheral nerve in order to block neurosensation. Neurostimulation has application for numerous debilitating conditions, including treatment-resistant depression, epilepsy, gastroparesis, hearing loss, incontinence, chronic, untreatable pain, Parkinson's disease, essential tremor and dystonia. Other applications where neurostimulation holds promise include Alzheimer's disease, blindness, chronic migraines, morbid obesity, obsessive-compulsive disorder, paralysis, sleep apnea, stroke, and severe tinnitus.

Today's pacing leads manufactured by St. Jude, Medtronic, and Boston Scientific are typically referred to as multifilar, consisting of two or more wire coils that are wound in parallel together around a central axis in a spiral manner. This construction technique helps to reduce impedance in the conductor, and builds redundancy into the lead in case of breakage. The filar winding changes the overall stress vector in the conductor body from a bending stress in a straight wire to a torsion stress in a curved cylindrical wire perpendicular to lead axis. A straight wire can be put in overall tension, leading to fatigue failure, whereas a filar wound cannot. However, the bulk of the wire and the need to coil or twist the wires to reduce stress, limit the ability to produce smaller diameter leads.

Modern day pacemakers are capable of responding to changes in physical exertion level of patients. To accomplish this, artificial sensors are implanted which enable a feedback loop for adjusting pacemaker stimulation algorithms. As a result of these sensors, improved exertional tolerance can be achieved. Generally, sensors transmit signals through an electrical conductor which may be synonymous with pacemaker leads that enable cardiac electrostimulation. In fact, the pacemaker electrodes can serve the dual functions of stimulation and sensing.

It is the object of the invention described herein to overcome the problems of previously available electrical conductors for implantable electrostimulation medical devices, as well as a wide spectrum of non-medical applications, where currently available electrical conductors are less than ideal.

SUMMARY OF THE INVENTION

In the invention of this patent application, a flexible and durable fine wire electrical conductor, termed a lead, for implanting in the body, is connected to a pacemaker, ICD, CRT or other cardiac pulse generator. The electrical conductor used to fabricate a lead is formed from a drawn silica, glass, or sapphire crystalline quartz fiber core, herein referred to collectively as a glass fiber, with a conductive metal buffer cladding on the core. This may include both medical and non-medical applications. For either a metallized glass or polymer fiber, the structure can also be enhanced by incorporating a polymer coating over the metal buffer cladding, which may provide a biocompatible surface resistant to environmental stress cracking or other mechanism of degradation associated with exposure and flexure within a biological system. In non-medical applications, the polymer coating may serve simply as an electrical insulation—a function shared with leads intended for medical applications.

In an alternative embodiment, a polymer fiber core is configured to serve as substrate for metallization instead of a glass fiber. In this embodiment, a relatively inelastic but flexible polymer is chosen such that the polymer fiber core is relatively resistant to tensile forces, but can bend in a manner to enable application in non-linear configurations. Metallization may be done on a polymer fiber during the process of creating the polymer core—typically extrusion. Alternatively, the polymer may be metallized in a separate step following extrusion. Hermetic sealing of the polymer core by metallization may or may not be necessary, depending on the polymer and intended application of the electrically conductive product. While various means of metallization suitable for polymer substrates are known in the art, those favored for this invention result in integration of the metal into the polymer surface in order to achieve desired adhesion of metal to the polymer. As for the case of glass fibers, metallization of polymer may involve initial laying down of one thin metal coating using a metal known to result in good adhesion of metal to polymer, followed by a second metal coating. In this approach, the first metal may or may not have good electrical conductivity, but its primary purpose is to provide a strong adhesion to polymer, and a metal surface suitable for laying down a second metal layer with desired electrical conductivity characteristics.

In additional embodiments, metals may be mixed directly with glass or silica or polymer core substrates to produce electrically conductive fibers.

The outer diameter of the electrical conductor preferably is less than about 750 microns, and may be 200 microns or even as small as 50 microns. Metals employed in the buffer can include aluminum, silver, gold, platinum, titanium, tantalum, gallium, or others, as well as metal alloys of which MP35N, a nickel-cobalt based alloy platinum-iridium, and gallium-indium are examples. In one embodiment the metal cladding is aluminum, silver, or gold, applied to the glass fiber core. This may include immediate application upon drawing the fiber, or may involve application of metal to a pre-formed glass fiber by one of several processes including chemical or physical vapor deposition, or electroplating. Metallization of the glass fiber provides a protective hermetic seal over the fiber surface. Alternatively, the glass fiber can be hermetically sealed with carbon or polymer following drawing of the fiber, the surface of which can then be metallized by one of the processes previously mentioned. This embodiment is further detailed below.

For applications in which delivery of high voltage or current is needed, multiple fibers can be used in parallel. For instance, for a metallized glass fiber of given length, say approximately 36 inches, and an overall electrical circuit of a given resistance, say 100 ohms, capable of supporting a 25 millisecond exponential pulse of 1500 volts, the peak current load would be 15 amps, based on Ohms law. If an electric pulse of greater amplitude is required, say 30 amps, then two or more metallized glass fibers can be electrically coupled in parallel to provide a current path capable of supporting an electric pulse of 30 amps.

Alternatively, the glass fiber can be fabricated as a dielectric with a metal wire in the center of the glass fiber core as one electrical conductor, and a metallic buffer layer applied on the outside of the glass fiber core, both protecting the fiber and acting as a coaxial second conductor or ground return.

In an additional embodiment, a further layer of silica, glass, etc. (as above) covers the metallic cladding, with a further electrically conductive buffer covering that dielectric layer. This embodiment may be with or without a center wire in the inner fiber. These silica, glass, etc. layers and buffer coatings can be continued for several more layers to produce a multiple conductor cable.

In a further embodiment the center of the fiber core is hollow to increase flexibility of a lead of a given diameter. In still a further embodiment, multiple conductors are embedded separately side-by-side in the glass fiber core, where the glass serves to electrically insulate the conductors from each other.

In an additional embodiment, an electrical conductor is composed of many smaller metal-buffered or metal wire-centered glass fibers that together provide the electrical connection. This embodiment allows for high redundancy for each connection and very high flexibility.

Additional embodiments differ from the aforementioned embodiments in that metal is not necessarily applied directly to the glass fiber. As mentioned previously, a non-metal buffer such as carbon and/or polymer may be applied directly to the glass fiber core to form a protective hermetic seal layer on the fiber. Metal can then be deposited upon the carbon and/or polymer in a subsequent step. Such a metal deposition process may conveniently take place through a batch process, or via a continuous deposition process, in which carbon- and/or polymer-coated fiber is moved continuously through a deposition chamber during the metal deposition process. Such metal deposition may be carried out by vapor deposition, electroplating—especially upon an electrically conductive carbon surface, by coating with an electrically conductive ink, or by one of numerous other metal deposition processes known in the art. In the case of vapor deposition and related processes governed by line-of-sight considerations, one or more metal targets—sources for vaporized metal, may be positioned within the metal deposition chamber in such a way as to insure overlap and complete 360 degree coverage of the fiber during the metal deposition process. Alternately, the fiber may be turned or rotated within the vapor deposition field to insure complete and uniform deposition. Vapor deposition processes are typically carried out in an evacuated chamber at low atmospheric pressure (approximately $1.0 \times 10^{-6}$ torr). After evacuation is attained, the chamber is back-filled with a plasma-forming gas, typically argon, to a pressure of $2.0 \times 10^{-3}$ torr. Masking may be pre-applied to the carbon and/or polymer surface to enable a patterned coating of metal on the carbon and/or polymer surface. Such a pattern may be useful for creating two or more separate electrically conductive paths along the length of the electrical conductor, thus enabling fabrication of a bipolar or multipolar conductor upon a single electrical conductor. Inherent in the concept of a metallized electrical conductor according to this invention is the ability to use more than one metal in the construction of such electrical conductors. For instance, an initial metal may be deposited on the basis of superior adhesion to the carbon and/or polymer underlayment. One or more additional metals or metal alloys could then be deposited on the first metal. Intent of the second metal would be to serve as the primary conductive material for carrying electrical current.

The completed metallized electrical conductor may then be conveniently coated with a thin polymeric material, such as Teflon to provide insulation and/or lubriciousness. Also, polyurethane or silicone or other insulative polymers may conveniently be used as jacketing material, providing biocompatibility and protection from the external environment. A coaxial iteration of this embodiment incorporating two independent electrical conductors may be constructed in which a metal electrical conductor is embedded within the central glass or silica core, with the second conductor being applied to the carbon and/or polymer buffer residing on the outer surface of the glass or silica core.

In an additional embodiment of metal cladding for the glass fiber, temporary sealing materials may be applied to the glass fiber for protection. Subsequent steps carried out in a controlled environment facilitate removal of the temporary sealing materials, followed by resurfacing the fiber with metal or other material, such as polymer or carbon. Such steps enable controlled metal surfaces to be applied directly to the glass fiber, if so desired. Temporary sealing materials may consist of polymers, carbon, or metals, which are chosen ease of removal. In the case of polymers, removal may be facilitated by dissolution in appropriate solvent, heat, alteration in pH or ionic strength, or other known means of control. Carbon and metals may be removed by chemical or electrochemical etching, heating, or other known means of control.

As indicated previously, various metals or metal alloys may be suitable for employment as a permanently deposited electrical conductor of this invention. Idealized properties include excellent electrical conductivity with low electrical resistance, resistance to corrosion, or heat, which may be employed at various steps during the electrical conductor manufacturing process. Additional resistance to exposure to cold, vacuum, vibration, and cyclic bending fatigue represent desired characteristics.

Estimated metal cross sectional area for a desired electrical resistance may be determined theoretically from the following relationship:

$$R=\rho*(1/A),$$

where R=resistance (ohms), $\rho$=metal resistivity (ohms-cm), 1=conductor length (cm) and A=cross sectional area of conductor. Thus, desired resistance is equal to the product of resistivity and the quotient of length and cross-sectional area. For some applications of the electrical conductor of this invention, desired electrical resistance may be on the order of 50 ohms. Using silver as an example, resistivity is $1.63\times10^{-6}$ ohms-cm. Thus, a silver conductor of approximately 1000 nm thickness would provide the desired electrical resistance for an electrical conductor of approximately 0.015 cm diameter and 80 cm length.

The electrical conductor of this invention, whether coaxial or otherwise in construction, is extremely strong and flexible. The invention contemplates cables (meaning glass fiber incorporating one or more electrical conductors) of as little as 100 to 200 micron diameter, or as large as 750 microns or more in diameter, and even unipolar electrical conductors as small as 50 microns in diameter or even smaller. These small diameter electrical conductors have significant flexibility with an achievable bend radius of less than 1 mm, to provide placement in tortuous tracts, as might be encountered in the heart in the case of pacemaker leads, or in fine electronic circuitry as might be incorporated in both medical and non-medical electrical instrumentation.

The multipolar electrical conductor representing one embodiment of this invention adapts technologies that have been developed for various disparate applications. Glass fiber is produced from a draw tower, a furnace that melts the silica or glass (or grown crystals for the sapphire and quartz) and allows the fiber to be pulled, "drawn", vertically from the bottom of the furnace. Fibers produced in this manner have strength of over 1 Mpsi. If the drawn fiber is allowed to sit in normal atmospheric conditions for more than a few minutes that strength will rapidly be reduced to the order of 2-10 kpsi. This reduction is caused by water vapor attack on the outer silica or glass surface, causing minute cracking. Bending the silica or glass fiber causes the outside of the bend to be put into tension and the cracks to propagate across the fiber causing failure. To ensure that the fiber remains at its maximum strength, a buffer is added to fibers as they are drawn. As the fiber is drawn and cools, a plastic coating, the buffer, is applied in a continuous manner protecting the fiber within a second of being produced. The TOW missile was developed during the 1960s as an antitank missile for the U.S. Army. The missile was launched from a shoulder mounted launcher and was guided to the target by an optical system that included a fiber spooled from the rear of the missile as it flew. The fiber had to be very strong and light to unreel several kilometers of fiber in a few seconds. Fiber optics was selected, but to further strengthen the fiber and protect it from damage, the plastic buffer was replaced with a metal buffer. The metal buffer used at that time was aluminum, but systems to coat fibers with gold and other metals have since been developed. The patents for the metal buffer technology covered a wide range of metals and alloys and were issued to Hughes in 1983 (U.S. Pat. Nos. 4,407,561 and 4,418,984).

The concept of using glass fibers incorporating optical capabilities in a coaxial construction was developed for micro miniature x-ray sources by Xoft, Inc., Photoelectron Corporation and others. See U.S. Pat. Nos. 6,319,188 and 6,195,411. These fibers were used because they provided high flexibility, high voltage hold-off and direct connection to the x-ray source without a joint between the x-ray source and the HV power supply. The standard available optical-capable fiber did not include a central electrical conductor. To include a wire in the center of the fiber, the wire must be drawn with the silica, glass, etc. in the draw tower. For optical applications, to ensure that any optical energy launched into the fiber is not absorbed at the core wire interface, an additional lower index silica or glass cladding is provided between the core and the wire. All this is known prior practice. The electrically conductive glass fiber of the invention of this application does not require an extra silica or glass cladding for use with non-optical electrical conduction.

Alternative methods of producing a coaxial electrically conductive glass fiber include drawing a core fiber, coating that core with a metal buffer and drawing additional silica or glass over the assembly and cladding that final assembly with an additional metal buffer. Fibers can be pulled with a hole in the center as well, increasing flexibility; hole diameter can vary. In one embodiment one or more wires can be put inside the hole through a fiber. The fiber can be redrawn to engage the wire if desired.

Additional embodiments can also be defined, where the glass fiber, either solid core or hollow, can act as the strength member and dual electrical conductors can be placed outside the fiber system and separated by plastic or polymer insulators. Fatigue of metals and plastics after millions of small deflection stresses is one of the life-limiting aspects of conventional wire constructions of conventional pacing leads and other conductors used for both medical and non-medical applications. Silica, glass, etc. fibers protected with robust buffer systems will not exhibit fatigue. Fatigue in silica or glass is caused by propagation of cracks, which are present at low levels in typical silica or glass fibers as produced for standard communication purposes. Typically they exhibit a few surface flaws per kilometer of fiber. Therefore silica or glass fiber coax cables make ideal pacing leads; small diameter, low mass, highly flexible, robust and with very long service life. Such attributes are also what make the glass fiber electrical conductor of the invention attractive for use in non-medical applications. Sophisticated electrical equipment represent a hallmark of the modern military force, and a small profile, lightweight, and durable electrical conductor, resistant to breakdown from heat, cold, environmental contamination, and/or solar exposure would have immediate usefulness across many possible scenarios. Examples include, but are not limited to, soldier interconnects, avionics, command and control, weapons, communication, data acquisition, and imaging. Multiple civilian applications can also be identified where the unique features of the invention can be applied. Examples include all motorized modes of transportation where a light durable electrical conductor is desired.

One method according to the invention for testing fibers intended for use in electrical conductors is to stretch a long segment until it breaks; the weakest point in the fiber will break first. If the fiber meets some minimal standard for tensile strength, then the entire fiber meets some strength minimum and flaws will not exist up to some level. If the fiber does break, the remaining pieces can be similarly tested. As this is repeated the limits at which the fiber will break will continue to climb allowing selection of extremely flaw free sections of fiber. This will further enhance the ability of the fiber to resist failure due to repeated stress cycling. This is a type of fiber "proofing", but proofing as previously known was for lot testing rather than for selections of sections of highest strength from a fiber. Pursuant to the invention fibers for use in the electrical conductors are proofed to at least about 90% of the intrinsic strength value of the material, or more broadly, at least about 75%.

The glass/silica electrical conductor of the invention, as envisioned for implantable electrostimulation medical devices, is compatible with drug/steroid elution for controlling fibrosis adjacent to a terminal electrode, which is a known technique used with conventional pacing leads for controlling impedance and thus battery life. For example, a biodegradable polymer can be positioned on the distal end of a lead at the terminal electrode, with the polymer containing the eluting drug.

It is among the objects of the invention to improve the durability, lifetime flexibility and versatility of wire leads for implantable electrostimulation medical devices such as pacemakers, ICDs, CRTs and other cardiac pulse generators, as well as electrostimulation or sensing leads for other therapeutic purposes within the body. It is also an object of the invention to reduce the weight and size associated with an electrical conductor over those of previously available electrical conductors, for applications where such characteristics are desired. Applications including medical and non-medical, military and civilian, terrestrial and aeronautic are all anticipated. These and other objects, advantages and features of the invention will be apparent from the following description of embodiments, considered along with the accompanying drawings.

DESCRIPTION OF THE DRAWINGS

FIG. 6 is a view showing an embodiment with twisted or braided multiple conductors.

FIG. 7 is a schematic perspective view showing another form of fine wire electrical conductor FIG. 8 is a sectional view showing a connector at an end of an electrical conductor of the invention.

DESCRIPTION OF PREFERRED EMBODIMENTS

The invention encompasses electrical conductors for all implantable electrostimulation and sensing devices having implanted wire leads, and non-medical applications where light weight and durability are important characteristics contributing to the performance of the electrical conductor, especially in extreme environmental conditions.

Figure 1:
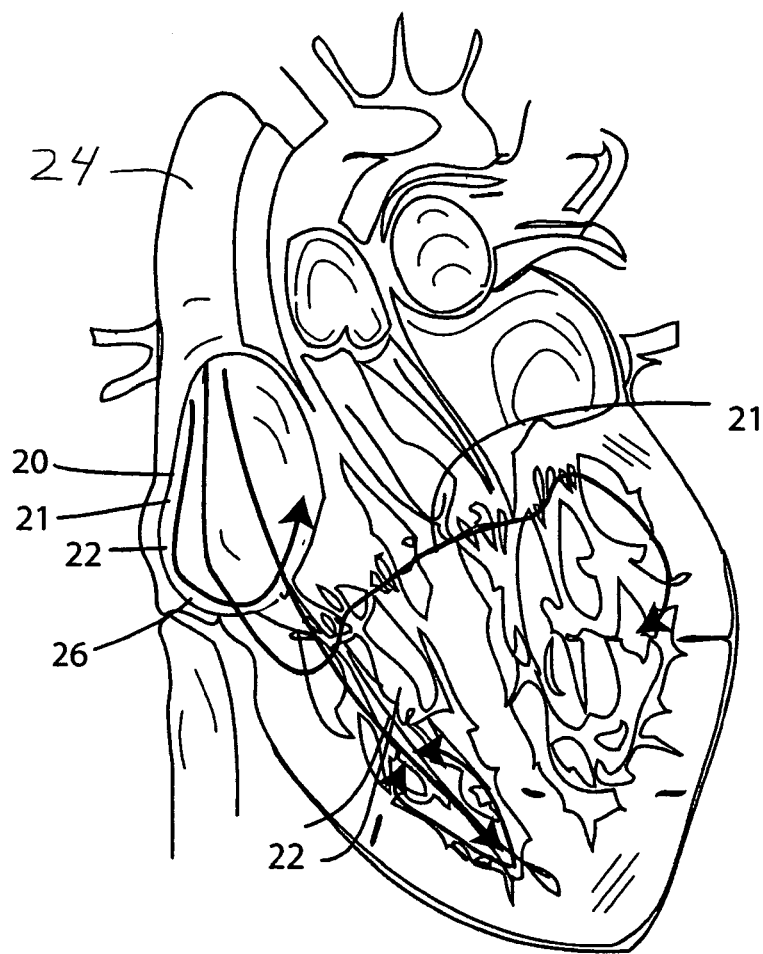
FIG. 1 is a schematic view partially cut away, showing a human heart, and indicating a path of pacemaker or other cardiac electrostimulation leads in accordance with conventional practice.

FIG. 1 shows schematically a human heart with some walls cut away. In FIG. 1 pacing leads are shown following a conventional path into the heart, and into the cardiac veins of the left ventricle, as has been typical of conventional practice and which, with some exceptions, is the basic path of leads of this invention.

In typical conventional practice, conductive leads 20, 21 and 22 are introduced into the heart through the superior vena cava 24, brought into the vena cava via subclavian or cephalic vein access points. For the right side of the heart, separate conventional pacing electrodes, as well as separate electrodes for biventricular pacing are normally routed into right ventricle, as well as the right atrium. For the left ventricle, typically a wire lead 21 would be brought from the right atrium 26 into the coronary sinus, and from there the leads are extended out into one or more coronary veins adjacent to the surface of the left side of the heart. The leads are not introduced directly into the interior of the left ventricle, which is the high-pressure chamber.

Pursuant to the invention the routing of silica/glass fiber leads can be essentially the same as with conventional leads. An important difference is that the silica/glass lead, being much smaller diameter than conventional leads, can be positioned deeper and more distally (also "retrograde" to normal blood flow toward the coronary sinus) within the target coronary vein. The coronary sinus/coronary vein architecture can be a relatively tortuous path, such that the physician will have an easier time manipulating a smaller diameter, flexible lead into the desired position within the coronary vein than for a larger diameter lead. Also, as a lead is manipulated deeper (more distally) within the coronary vein, the diameter of the vein becomes progressively narrowed. Thus, a smaller diameter lead can be placed deeper than a larger diameter lead. One theoretical reason why it is useful to place the terminal electrode of the lead in the deeper/distal/narrower portion of the coronary vein is that that portion of the vein apparently lies closer to myocardium. Thus, the cardiac muscle can perhaps be stimulated with less energy use when the electrode is closer to intimate contact with muscle overlying the coronary vein.

Figure 2:
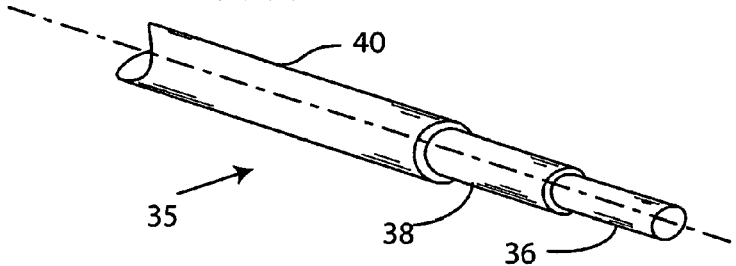
FIG. 2 is a schematic drawing in perspective showing one embodiment of an electrical conductor as intended for use in extreme environmental conditions.

FIG. 2 is a simple schematic showing one preferred embodiment of an implantable electrical conductor 35 pursuant to the invention. In this form the electrical conductor 35 is unipolar. It has a drawn fiber core 36 of glass, silica, sapphire or crystalline quartz ("glass/silica" or "silica/glass") with a conductive metal buffer 38 over the fiber core. As discussed above, in this embodiment, the buffer 38 is coated directly onto the fiber immediately upon drawing of the fiber, to preserve the strength of the fiber, protecting it from environmental elements such as atmospheric moisture that can attack the glass/silica surface and introduce fine cracking. Aluminum, silver, or gold are preferred metals to form the buffer 38 because of abilities to achieve hermetic bonding with the silica or glass surface, although other suitable metals or metal alloys can be used. The metal or metal alloy buffer can be about 20 microns thick, or 5 microns thick or even thinner. The wire lead 35 will make separate electrical connections (not shown) at either end.

FIG. 2 also shows a polymer coating 40 as an outer buffer. This buffer is also added very soon after drawing, and is applied after the metal buffer 38 in a continuous manner. The plastic outer buffer coating 40 may be biocompatible—for intended medical uses. Likewise, biocompatibility is likely not required for most non-medical applications. Other desired characteristics of the polymer layer include being impervious to sunlight, dust, water, and exposure to cold or heat, within the intended range of operating temperatures, where the range of temperatures may be between about −65° C. to about +170° C. As discussed further below, a further metal buffer can be added over the metal buffer 38 prior to addition of the plastic coating. This can be a coating of gold or platinum, both of which are biocompatible, or some other metal or metal alloy, such as gallium, gallium-indium, or MP35N. The plastic buffer 40 adds a further protective layer.

Figure 3:
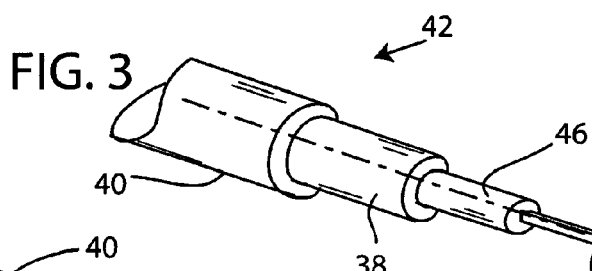
FIG. 3 is a similar view showing another embodiment of an electrical conductor.

FIG. 3 shows a modified fine wire electrical conductor 42, which has a metal conductor 44 as a center element. Here, the pure silica/glass fiber core 46 is drawn over the metal conductor 44.

The process is well known, with a hollow glass/silica fiber first produced, then a metal conductive wire placed through the hole in the fiber and the glass/silica fiber drawn down against the wire. A conductive metal buffer is shown at 38 over the fiber, having been applied immediately on drawing of the conductor-containing fiber 46. An outer buffer coating of polymer material is shown at 40, which may or may not be biocompatible, depending on the service environment of the electrical conductor.

Figure 4:
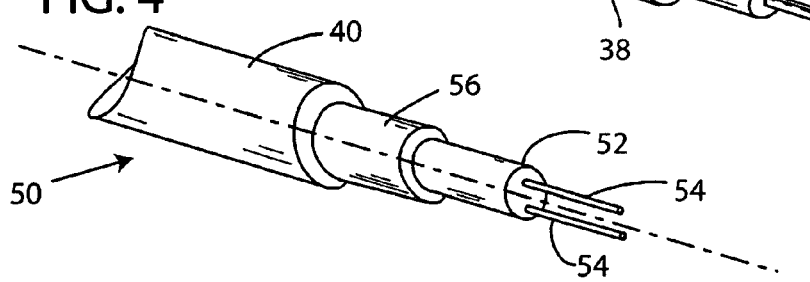
FIG. 4 is a view showing a further embodiment of an electrical conductor.

FIG. 4 is a similar view, but in this case showing a fine wire electrical conductor 50 formed of a glass/silica fiber core 52 formed over two metal conductors 54. The wire is pre-coated with a thin layer of glass before being co-drawn with fiber. A metal buffer coating 56 surrounds the silica fiber 52, protecting the fiber from deterioration as noted above, and this can serve as a third electrically conducting element if desired. Again, an outer polymer buffer 40 provides an outer protective jacket and may be biocompatible.

Figure 5:
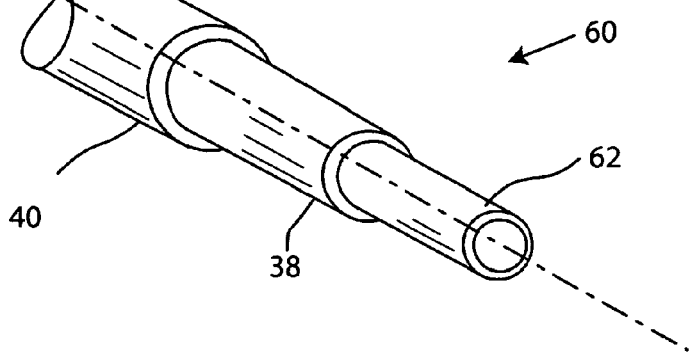
FIG. 5 is a view showing another embodiment of an electrical conductor.

In FIG. 5 is shown another embodiment of a fine wire electrical conductor 60 of the invention. In this case the glass/silica fiber core 62 is hollow, allowing for better flexibility of the electrical conductor of a given diameter, and the electrical conductor construction is otherwise similar to that of FIG. 2.

FIG. 6 shows a modified embodiment of a fine wire electrical conductor 65 which has multiple glass/silica fiber electrically conductive components 66 and 68 in a helical interengagement, twisted together. Each electrically conductive component 66, 68 comprise a glass/silica fiber conductor which can be similar to what is shown in FIG. 2, with or without a polymer buffer coating 40, or each could be constructed in a manner similar to FIG. 3, with or without a plastic buffer coating. Although two such fiber electrical conductors are shown, three or more could be included. The glass/silica fiber cores provide for strength and small-radius bending of the helical electrically conductive components 66, 68, and this type of braiding or helical twisted arrangement is known in the field of electrostimulation medical devices, and is intended for absorbing stretching, compression, or bending in a flexible manner. An outer polymer coating 70 protects the assembled electrically conductive components and provides biocompatibility, if so desired. The electrically conductive components 66, 68 themselves can have a single metal cladding, consisting of aluminum, silver, or gold, or other metal as their outer layer, or they can have one or more further layers of metal, glass and polymer.

FIG. 7 shows a section of an electrical conductor 72, which is similar to that of FIG. 2, with a silica core 36 and an initial metal cladding 38, but with a further metal cladding 74 over the inner metal cladding. Use of two dissimilar metals in direct physical contact is intended to take advantage of a first metal having desired bonding characteristics to the silica or glass core, with a second metal having desired electrical conductivity characteristics, and having durable bonding behavior on the first metal. The outer layer of polymer material is shown at 40.

FIG. 8 shows one example of a terminal or connector 75 of the invention, coupled to one end of two silica/glass fiber electrical conductors 76 and 78, each of which may be formed as described above, with a conductive buffer 80 on the exterior of each. FIG. 8 represents a biaxial pair of electrical conductors making electrical connection with two separate electrically conducting components of a terminal connector, respectively. In the type of connector 75 shown in FIG. 8, the glass/silica fibers 82 of each of the separate electrical conductors 76 and 78 extend into the connector as shown. A high temperature wire 84, 86, such as fabricated of Kovar—having thermal expansion characteristics similar to glass, is welded to each of the conductive buffer claddings 80 of the two electrical conductors 76 and 78, respectively. This welded connection is made essentially outside the terminal 75, to the right as viewed in FIG. 8, where the cladding 80 on the terminal ends of the electrical conductors will not be oxidized or rendered non-conductive by the formation of the terminal or connector. These wires are connected to respective ones of two electrically isolated sections 88 and 90 of the terminal. The two sections 88 and 90 are of conductive metal and are adapted to plug into a socket formed to receive this connector 75. Alternatively (not shown), a uniaxial connection between a single electrical conductor 76, 78 and a terminal connector with incorporating a single electrically conductive element may be envisioned.

Again referring to FIG. 8, inside the connector 75, the fibers and conductive wires 84, 86 are sealed within the connector portion 88 using a relatively low temperature glass 92. The connector wires 84, 86, if of material such as Kovar, will not deteriorate even if a high temperature glass is used for sealing. The glass seal 92 does not extend over the weld connection from the wires 84, 86 to the buffer 80 on each of the electrical conductive elements 76 and 78. These weld connections and the unprotected portions of the wires 84, 86 need to be protected, covered by an appropriate material at the back end of the connector 75, where the two electrical conductor components 76 and 78 emerge from the connector. They can be covered by a polymer, or more preferably a metal buffer can be applied to each individual wire/buffer 80 connection. This could be done before or after sealing with the glass seal 92. If a high temperature transition metal such as platinum is used for this purpose, the connection between the Kovar wire and the fiber could be protected from a high temperature glass seal 92, assuming a high temperature material is used here, in the case where the glass seal 92 is applied after the Kovar wire connection is made to the fiber. In this way a hermetic seal is achieved. As indicated, analogous terminal connectors can be formed on unipolar, single-fiber electrical conductors or on bipolar electrical conductors having an exterior conductive buffer and an interior wire.

Figure 9:
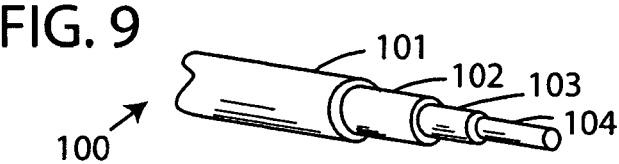
FIG. 9 is a schematic drawing in perspective showing another embodiment of an electrical conductor.

FIG. 9 represents a fine wire lead 100 in which metal 102 is deposited directly onto carbon hermetic seal material 103 overlying the glass/silica fiber core 104. Upon the metal layer, a polymer-based insulator 101 is applied. This insulator may be Teflon, or other lubricious polymer coating that is ideally resistant to mechanical- or friction-based wear or degradation with resultant cracking or physical loss from the fine wire lead. The carbon layer is relatively thin in profile, consisting generally of 10-1000 Angstroms in thickness. The metal layer may be on the order of 0.1-10 microns in thickness. The outer insulator does not require significant thickness for low-current applications as envisioned by this invention and thus may be 1-10 microns in thickness.

The carbon hermetic seal layer 103 can be deposited onto the glass/silica fiber core by any of several known techniques, such as plasma enhanced chemical vapor deposition using methane and hydrogen as the precursor gases. As reported in "Effects of annealing on the properties of hermetically carbon-coated optical fibers prepared by plasma enhanced chemical vapor deposition method", *Opt. Eng.*, Vol. 46, 035008 (2007); doi: 10.1117/1.2716015, Mar. 21, 2007, incorporated herein by reference, annealing temperature is important in this process.

A related iteration (not shown) incorporates a polymer layer in direct contact with the glass core 104, as a substitution for the carbon hermetic seal material 103. As an alternate to the lubricious polymer insulator 101, a polymer insulator with optimized biocompatibility such as polyurethane or silicone may be utilized.

Figure 10:
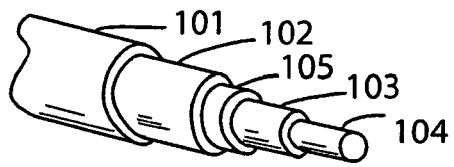
FIG. 10 is a similar view showing another embodiment of an electrical conductor.

FIG. 10 is similar to the fine wire lead depicted FIG. 9, with the incorporation of an additional polymer layer 105. This polymer resides between the metal hermetic seal material 103, and the conductive metal layer 102. This polymer layer 105 can provide protection to the carbon layer 103, as well as an improved bonding surface for metal deposition. The layer 103 could alternatively be a metal layer.

Figure 11:
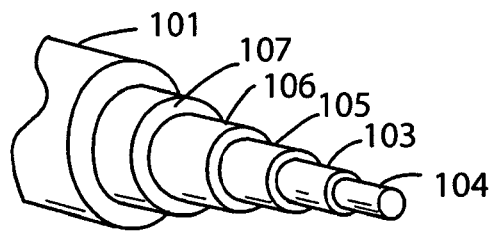
FIG. 11 is a view showing a further embodiment of an electrical conductor.

FIG. 11 is also similar to the fine wire lead in FIG. 9. In this case two separate metals 106 and 107 are deposited on a polymer clad material 105. The two separate metals can serve different functions, including optimization of tensile strength, crack resistance, electrical conductivity, and adhesiveness to underlying materials. Related iterations (not shown) being similar to FIGS. 9 and 10, would include more than two metal layers, and/or a carbon hermetic seal material 103 but no polymer cladding 105 or a polymer clad material 105 but no carbon layer 103.

Figure 12:
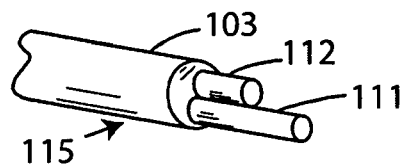
FIG. 12 is a view showing electrical conductor with multiple conductors.

FIG. 12 represents a fine wire lead with two conductive glass fibers 111 and 112, where each individual glass fiber reflects construction details according to previous figures, including individual glass/silica cores, hermetic seal materials of carbon and/or polymer, metal deposition, and polymer insulation. A single multiconductor fine wire lead 115 is thus fabricated by jacketing two or more conductive glass fibers within a single outer polymer jacket 103. This jacket is conveniently fabricated of biocompatible material such as polyurethane or silicone.

Figure 13:
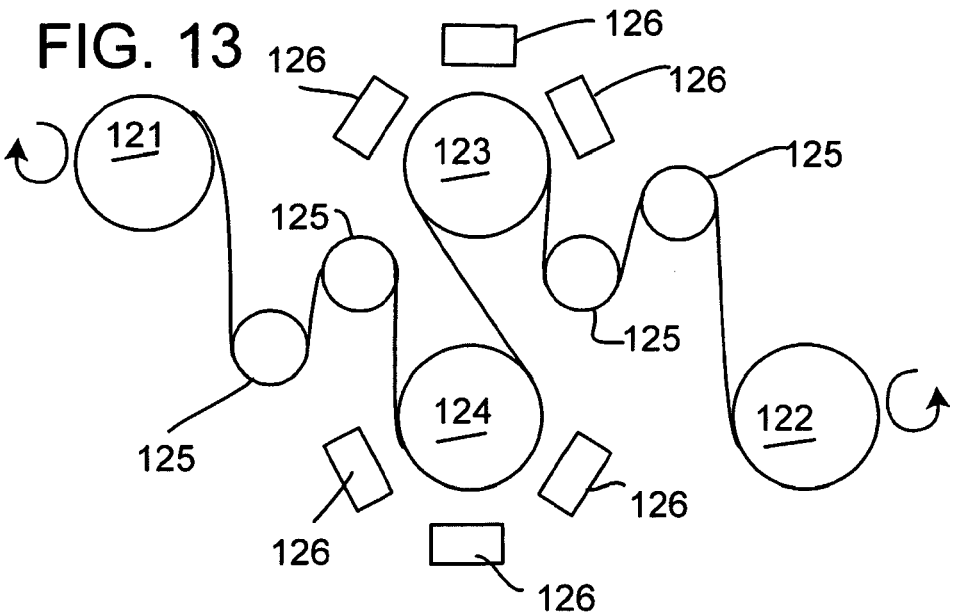
FIG. 13 is a depiction of a mechanism and movement path for continuous processing of an electrical conductor for metal deposition.

FIG. 13 is a depiction of a mechanism and movement path for continuous processing of a fine wire lead for metal deposition. The metal deposition process is designed to take place within a vacuum chamber in which gas composition and pressure may be controlled. Various motor-driven rollers 121-125 are set to provide directionality, tension, positioning, and duration of glass fiber substrate within the metal deposition field. At 121 is a feed roller, and at 122 a take-up roller. Chill drums are at 123 and 124. Metal source targets 126 are positioned within the chamber to provide adequate coverage of the glass substrate. Actual position of the metal source targets may or may not be directly adjacent to rollers within the chamber.

Figure 14A:
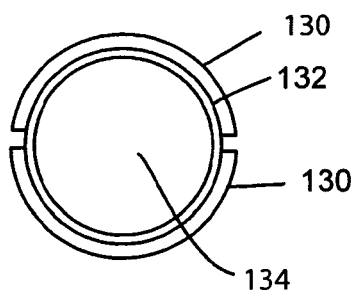
FIG. 14A is a cross sectional view of a possible patterned metal deposition on an electrical conductor(s).
Figure 14B:
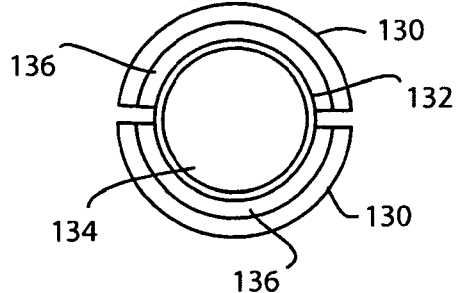
FIG. 14B is a cross sectional view of a possible patterned metal deposition on an electrical conductor(s).
Figure 14C:
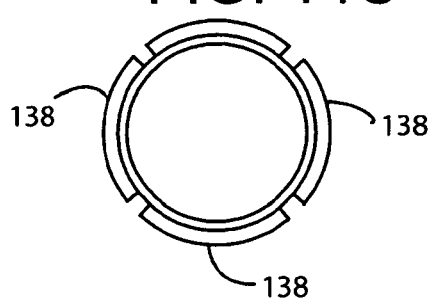
FIG. 14C is a cross sectional view of a possible patterned metal deposition on an electrical conductor(s).

FIGS. 14A-14C are a series of cross sectional views of several possible patterned metal depositions on fine wire leads. These depositions are conveniently carried out using masks in order to produce two or more independent electrically conductive paths down the length of the fine wire lead. Depicted are patterns involving two or four electrically conductive paths, made up of a single metal deposition, but may also represent deposition of two separate metals as in FIG. 14B. FIG. 14A shows two metal segments 130 in a single layer over a polymer buffer cladding 132 on a central core 134. In FIG. 14B two metal layers 130 and 136 form the two segments. In FIG. 14C four different metal segments 138 are shown, in a single layer.

Figure 15A:
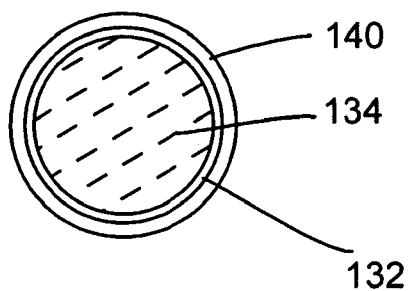
FIG. 15A is a cross sectional view of a possible electrical conductor having a single continuous metal electrical conductor.
Figure 15B:
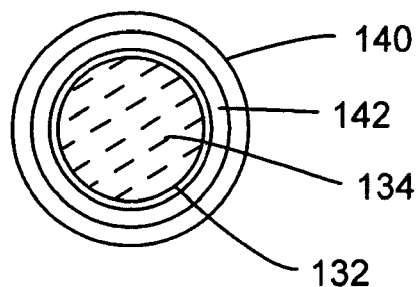
FIG. 15B is a cross sectional view of a possible electrical conductor having a single continuous metal electrical conductor.

FIGS. 15A and 15B show cross sectional views of two possible fine wire leads having a single continuous metal electrical conductor 140. The two cross sections differ in that one (FIG. 15A) incorporates a single metal 140 in the conductor, while the other (FIG. 15B) depicts a cross section in which two separate metals 140 and 142 are incorporated in a single electrical conductor. In both cases the metal is over a polymer buffer cladding 132, which covers a fine glass fiber core 134, preferably a thin hermetic or non-hermetic coated glass core. The two metals in FIG. 15B differ on the basis of fatigue resistance, electrical resistance, as well as other properties which might include heat conductance, melting point, and adhesion to underlying materials. The inner layer 142 can be a lower electrical resistance metal, while the outer layer 140 can be a high mechanical fatigue resistance metal.

Figure 16A:
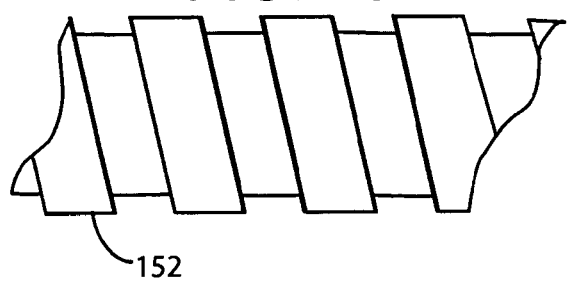
FIG. 16A is a schematic perspective showing an electrode deposition pattern made up of one or two metal electrical conductors. The electrical conductor may also incorporate a metal conductor at the center of the glass fiber core, resulting in a coaxial construction.
Figure 16B:
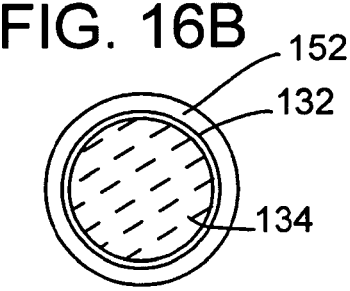
FIG. 16B is a cross sectional view showing an electrode deposition pattern made up of one or two metal electrical conductors. The electrical conductor may also incorporate a metal conductor at the center of the glass fiber core, resulting in a coaxial construction.
Figure 16C:
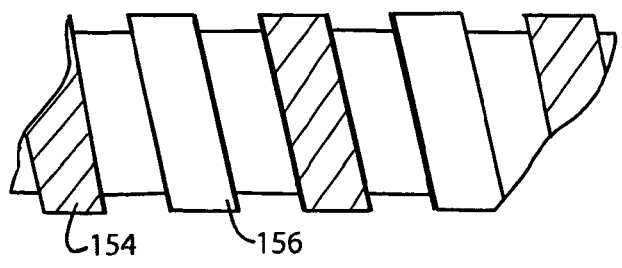
FIG. 16C is a schematic perspective showing an electrode deposition pattern made up of one or two metal electrical conductors. The electrical conductor may also incorporate a metal conductor at the center of the glass fiber core, resulting in a coaxial construction.
Figure 16D:
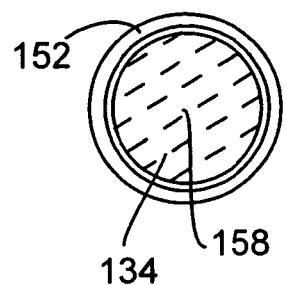
FIG. 16D is a cross sectional view showing an electrode deposition pattern made up of one or two metal electrical conductors on a electrical conductor. The electrical conductor may also incorporate a metal conductor at the center of the glass fiber core, resulting in a coaxial construction.

FIGS. 16A-16D are a series of schematic side and cross sectional views showing an electrode deposition pattern made up of one or two metal electrical conductors on a fine wire lead. In FIG. 16A a pattern 150 has a single metal 152 coated in a helical pattern on a glass fiber surface. FIG. 16B shows the lead in cross section and shows the glass core 134 can have a polymer buffer cladding 132. Masking may be used to enable patterned conductors as helical paths as shown, or other patterns. FIG. 16C shows a pattern with two isolated conductors 154 and 156 in helical configuration. Coaxial leads may also be constructed as depicted in the cross section of FIG. 16D, in which a metal lead 158 is deposited in the center of the glass core 134.

Figure 17:
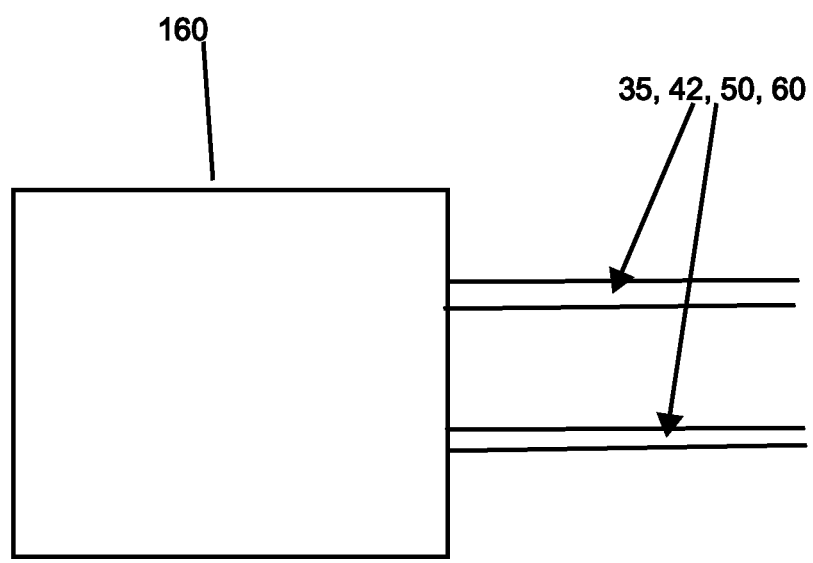
FIG. 17 is a schematic diagram indicating a fine wire conductor constructed in accordance with the invention and used in an extreme environment such as one involving repeated bending or vibration.

FIG. 17 is a simple schematic representation indicating one or two durable fine wire conductors 35, 42, 50, 60 or others described above, connected to a mechanical device 100. As explained above, the mechanical device 100 represents some form of extreme environment within which the fine wire conductor is placed. This can be a mechanical device exhibiting strong vibration, a satellite for delivery into orbit, an airplane or aerospace vehicle or other devices as described above. Durable fine wire conductors are only schematically illustrated and may be wholly contained within the device or vehicle 100, although they could also be electrical leads connected to and extending from a vibrating device. In the case of an airplane or aerospace vehicle the fine wire conductors can save considerable weight while still exhibiting flexibility and resistance to repeated bending or vibration when needed. The device, vehicle or object 100 can also represent other types of extreme environment within which the durable fine conductor 35, 42, etc. will resist corrosion or other deterioration.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:
1. An apparatus comprising:
    an electro-mechanical device configured and arranged to exhibit or experience movement; and
    a fine wire conductor including
        a drawn glass or silica fiber core;
        a first inner layer comprised of a polymer configured and arranged to provide a seal on the drawn glass or silica fiber core;
        a conductive metal buffer cladding on the polymer layer; and
    the fine wire conductor having an outer diameter at the conductive metal buffer cladding no greater than approximately 750 microns and being configured and arranged to provide an electrical pathway to the electro-mechanical device so as to carry an electrical current and to be sufficiently flexible for accommodating the movement.

2. The apparatus of claim 1, further comprising a second inner layer, the second inner layer positioned between the first inner layer and the core.

3. The apparatus of claim 2, wherein the first and second inner layers provide a hermetic seal on the drawn glass or silica fiber core.

4. The apparatus of claim 2, wherein the first or second inner polymer layer is formed from carbon.

5. The apparatus of claim 1, wherein the electrical pathway is a coaxial pathway.

6. The apparatus of claim 1, wherein the fine wire conductor is flexible to bend to a radius of about 8 to 10 times the fiber core diameter without damage.

7. The apparatus of claim 1, further comprising a first outer polymer coating outside the conductive metal buffer cladding, a second conductive metal buffer cladding on the first outer polymer coating, and a second outer polymer coating on the second conductive metal buffer cladding.

8. The apparatus of claim 7 wherein the second metal buffer cladding is of a different thickness than the first metal buffer cladding.

9. The apparatus of claim 1, wherein the glass fiber core is an optical capable glass fiber.

10. The apparatus of claim 1, wherein the glass or silica fiber core comprises silica.

11. The apparatus of claim 1, wherein the metal buffer cladding is selected from the group consisting of aluminum, silver, or gold.

12. The apparatus of claim 1, wherein the buffer cladding is between 200 nm thick and 40 microns thick.

13. The apparatus of claim 1, wherein the metal buffer cladding is patterned to produce multiple discrete conductive paths on the same metal layer.

14. The apparatus of claim 13, wherein the metal buffer cladding comprises two electrically conductive paths.

15. The apparatus of claim 13, wherein the metal buffer cladding consists of four electrically conductive paths.

16. The apparatus of claim 1, wherein the metal buffer cladding comprises a helical pattern.

17. The apparatus of claim 1, wherein the fine wire conductor includes a plurality of said glass or silica fiber cores each with a metal buffer cladding, combined together in the fine wire conductor.

18. The apparatus of claim 1, wherein the metal buffer cladding comprises two separate metals in a single conductor.

19. An apparatus comprising:
- an electro-mechanical device configured and arranged to exhibit or experience movement; and
- a fine wire conductor including
  - a drawn glass or silica fiber core;
  - a first inner polymer layer configured and arranged to provide a seal on the drawn glass or silica fiber core;
  - a conductive metal buffer cladding on the polymer layer; and
- the fine wire conductor having an outer diameter at the conductive metal buffer cladding no greater than approximately 750 microns and being configured and arranged to provide an electrical pathway and an optical pathway to the electro-mechanical device so as to carry an electrical current and an optical signal and to be sufficiently flexible for accommodating the movement.

20. The apparatus of claim 19, wherein the fine wire conductor includes a plurality of said glass or silica fiber cores each with a metal buffer cladding, combined together in the fine wire conductor.

* * * * *